United States Patent
Tsuji et al.

(10) Patent No.: US 11,497,778 B2
(45) Date of Patent: *Nov. 15, 2022

(54) COMPOSITION FOR IMPROVING SKIN CONDITIONS

(71) Applicant: Kirin Holdings Kabushiki Kaisha, Tokyo (JP)

(72) Inventors: Ryohei Tsuji, Tokyo (JP); Munekimi Nanao, Tokyo (JP); Toshio Fujii, Tokyo (JP); Takeshi Kokubo, Tokyo (JP)

(73) Assignee: Kirin Holdings Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/980,714

(22) PCT Filed: Mar. 15, 2019

(86) PCT No.: PCT/JP2019/010773
§ 371 (c)(1),
(2) Date: Sep. 14, 2020

(87) PCT Pub. No.: WO2019/177139
PCT Pub. Date: Sep. 19, 2019

(65) Prior Publication Data
US 2021/0008127 A1    Jan. 14, 2021

(30) Foreign Application Priority Data
Mar. 15, 2018  (JP) .............................. JP2018-048311

(51) Int. Cl.
*A61K 35/744* (2015.01)
*A61K 39/09* (2006.01)
*A61K 35/00* (2006.01)
*A61K 9/00* (2006.01)

(52) U.S. Cl.
CPC .......... *A61K 35/744* (2013.01); *A61K 9/0056* (2013.01); *A61K 39/09* (2013.01); *A61K 2035/115* (2013.01)

(58) Field of Classification Search
None
See application file for complete search history.

(56) References Cited

U.S. PATENT DOCUMENTS

| | | |
|---|---|---|
| 2012/0121685 A1 | 5/2012 | Mercenier et al. |
| 2013/0095073 A1 | 4/2013 | Masuoka et al. |
| 2017/0189327 A1 | 7/2017 | Chae et al. |
| 2018/0311341 A1 | 11/2018 | Suzuki et al. |
| 2020/0179463 A1 | 6/2020 | Tsuji et al. |

FOREIGN PATENT DOCUMENTS

| | | |
|---|---|---|
| JP | 2006-069940 A | 3/2006 |
| JP | 2013-526265 A | 6/2013 |
| JP | 2013-233097 A | 11/2013 |
| JP | 2017-081838 A | 5/2017 |
| JP | 2017-534589 A | 11/2017 |
| WO | WO-2009/066537 A1 | 5/2009 |
| WO | WO 2012/091081 A1 * | 7/2012 |
| WO | WO-2018/051895 A1 | 3/2018 |

OTHER PUBLICATIONS

Kimoto-Nira et al. J. Nutritional Science, vol. 1, e18, pp. 1-7, 2012.*
International Preliminary Report on Patentability dated Sep. 15, 2020 in PCT/JP2019/010773, with English translation.
International Search Report dated Apr. 16, 2019, in PCT/JP2019/010773.
Supplementary European Search Report dated Dec. 6, 2021 in EP 19767482.3.

* cited by examiner

*Primary Examiner* — S. Devi
(74) *Attorney, Agent, or Firm* — Foley & Lardner LLP

(57) ABSTRACT

An object of the present invention is to provide a novel food material effective for improving skin conditions. The present invention provides a composition for use in improving skin conditions, comprising a *Lactococcus* bacterium as an active ingredient. Examples of the *Lactococcus* bacterium include *Lactococcus lactis*. The skin conditions are skin conditions deteriorated by light exposure, such as an increase in skin redness and a decrease in skin moisture content.

14 Claims, 2 Drawing Sheets

COMPOSITION FOR IMPROVING SKIN CONDITIONS

CROSS-REFERENCE TO RELATED APPLICATION

The present application is the U.S. National Stage of PCT/JP2019/010773, filed Mar. 15, 2019, which enjoys the benefit of priority from the prior Japanese Patent Application No. 2018-48311 filed on Mar. 15, 2018, the entire disclosure of which is incorporated herein by reference.

TECHNICAL FIELD

The present invention relates to a composition for improving skin conditions.

BACKGROUND ART

The skin is composed of epidermis, dermis, and subcutaneous tissue from the outside, and is responsible for retaining moisture in the body and protecting the living body from invasion of physical and chemical stimuli and pathogenic microorganisms. The epidermis is classified into stratum basale, stratum spinosum, stratum granulosum, and stratum corneum, from the deep layer toward the surface layer. In the stratum corneum, corneal cells pile up in several to several dozen layers to form a strong corneal barrier, which retains moisture and protects the skin from drying and external stimuli. It is said that a decrease in moisture content of the stratum corneum due to external factors such as drying and ultraviolet light, as well as internal factors such as aging, senility, internal diseases and stress lowers the barrier function of the skin and increases the sensitivity to external stimuli, so that external stimuli such as ultraviolet light and allergens are likely to invade, resulting in not only a dry state but also deterioration of various skin conditions.

Ultraviolet light is classified into UVA, UVB and UVC according to the wavelength. UVB passes through the epidermis and reaches the upper dermis, and UVA reaches the lower dermis. Sunburn caused by UVB irradiation begins several hours after exposure and peaks after 24 hours, and causes mild burning sensation and erythema in a mild case, and causes edema, blisters and dark red spots with erosion, associated with a strong burning sensation in an advanced case. In skin tissues with erythema, dilatation of blood capillaries in the upper dermis and swelling of vascular endothelial cells are observed. It is desirable that deterioration of skin conditions caused by drying and ultraviolet light is improved in an early phase, from the viewpoint of both recovery to normal skin functions and beauty.

Food materials of natural origin regarded as being effective for improving skin functions have been proposed so far. As a food material of microbial origin, a fermented milk product with a lactic acid bacterium belonging to *Lactococcus lactis* is known to have a skin function improvement effect (Patent Document 1). However, the technique of Patent Document 1 is intended to prevent and reduce a stress-induced decrease in skin blood flow, not to improve skin functions deteriorated due to ultraviolet disorders.

REFERENCE LIST

Patent Documents

Patent Document 1: JP 2006-69940 A

SUMMARY OF THE INVENTION

An object of the present invention is to provide a novel food material effective for improving skin conditions.

The present inventors have now found that *Lactococcus lactis* subsp. *lactis* JCM5805, which is one type of *Lactococcus* bacteria, has an effect for improving skin conditions in mice and humans. The present invention is based on these findings.

The present invention provides the following inventions.

[1] A composition for use in improving skin conditions and an agent for improving skin conditions, each comprising a *Lactococcus* bacterium as an active ingredient.

[2] The composition and agent according to [1], wherein the skin conditions are skin conditions deteriorated by light exposure.

[3] The composition and agent according to [1] or [2], wherein the skin conditions deteriorated by light exposure are a decrease in skin moisture content and/or an increase in skin redness.

[4] The composition and agent according to any one of [1] to [3], which each comprise the *Lactococcus* bacterium in the form of a dead bacterium.

[5] The composition and agent according to any one of [1] to [4], wherein the *Lactococcus* bacterium is *Lactococcus lactis*.

[6] The composition and agent according to any one of [1] to [5], wherein the *Lactococcus* bacterium is *Lactococcus lactis* subsp. *lactis* JCM5805.

[7] The composition and agent according to any one of [1] to [6], which each comprise an effective daily intake amount for a human of the *Lactococcus* bacterium.

[8] The composition and agent according to [7], wherein the effective daily intake amount for a human ranges from 0.5 to 1000 mg on the basis of dried bacterial powder.

[9] The composition and agent according to [7], wherein the effective daily intake amount for a human ranges from $1 \times 10^8$ to $1 \times 10^{14}$ on the basis of the number of bacteria.

[10] The composition and agent according to any one of [1] to [9], which are each in the form of a unit package.

[11] The composition and agent according to any one of [1] to [10], which are each a food composition.

[12] A method for improving skin conditions, comprising feeding or administering an effective amount of a *Lactococcus* bacterium or a composition comprising the same to a subject in need thereof.

[13] Use of a *Lactococcus* bacterium or a composition comprising the same, for the manufacture of an agent for improving skin conditions, as an agent for improving skin conditions, or in the method according to [12].

[14] A *Lactococcus* bacterium or a composition comprising the same, for use in improving skin conditions or for use in the method according to [12].

[15] A composition for use in treating, preventing and improving photodermatosis and an agent for treating, preventing and improving photodermatosis, each comprising a *Lactococcus* bacterium as an active ingredient.

[16] A method for treating, preventing and improving photodermatosis, comprising feeding or administering an effective amount of a *Lactococcus* bacterium or a composition comprising the same to a subject in need thereof.

[17] Use of a *Lactococcus* bacterium or a composition comprising the same, for the manufacture of an agent for treating, preventing or improving photodermatosis, as an agent for treating, preventing or improving photodermatosis, or in the method according to [16].

[18] A *Lactococcus* bacterium or a composition comprising the same, for use in treating, preventing or improving photodermatosis or for use in the method according to [16].

In the present specification, the compositions according to [1] and [15] are each referred to as the "composition of the present invention" and the agents according to [1] and [15] are each referred to as the "agent of the present invention," in some cases.

The composition and agent according to the present invention each comprise, as an active ingredient, a lactic acid bacterium which is a food material that has been eaten by humans for a long time. Accordingly, the composition and agent according to the present invention are advantageous in that they can be used for improving skin conditions and can be ingested over a long time without concerns about side effects.

DETAILED DESCRIPTION OF THE INVENTION

The *Lactococcus* bacterium used as an active ingredient in the present invention is a lactic acid coccus belonging to the genus *Lactococcus*. *Lactococcus* bacteria include *Lactococcus lactis* subsp. *lactis*, *Lactococcus garvieae*, *Lactococcus lactis* subsp. *cremoris* and *Lactococcus lactis* subsp. *hordniae*, and is preferably *Lactococcus lactis* subsp. *lactis*.

Specific examples of *Lactococcus* bacteria include *Lactococcus lactis* subsp. *lactis* JCM5805, *Lactococcus lactis* subsp. *lactis* JCM20101, *Lactococcus lactis* subsp. *lactis* NBRC12007, *Lactococcus lactis* subsp. *lactis* NRIC1150, *Lactococcus garvieae* NBRC100934, *Lactococcus lactis* subsp. *cremoris* JCM16167, *Lactococcus lactis* subsp. *cremoris* NBRC100676, *Lactococcus lactis* subsp. *hordniae* JCM1180, and *Lactococcus lactis* subsp. *hordniae* JCM11040. *Lactococcus lactis* subsp. *lactis* JCM5805 and *Lactococcus lactis* subsp. *lactis* JCM20101 are preferred, and *Lactococcus lactis* subsp. *lactis* JCM5805 is particularly preferred.

Figure 1:
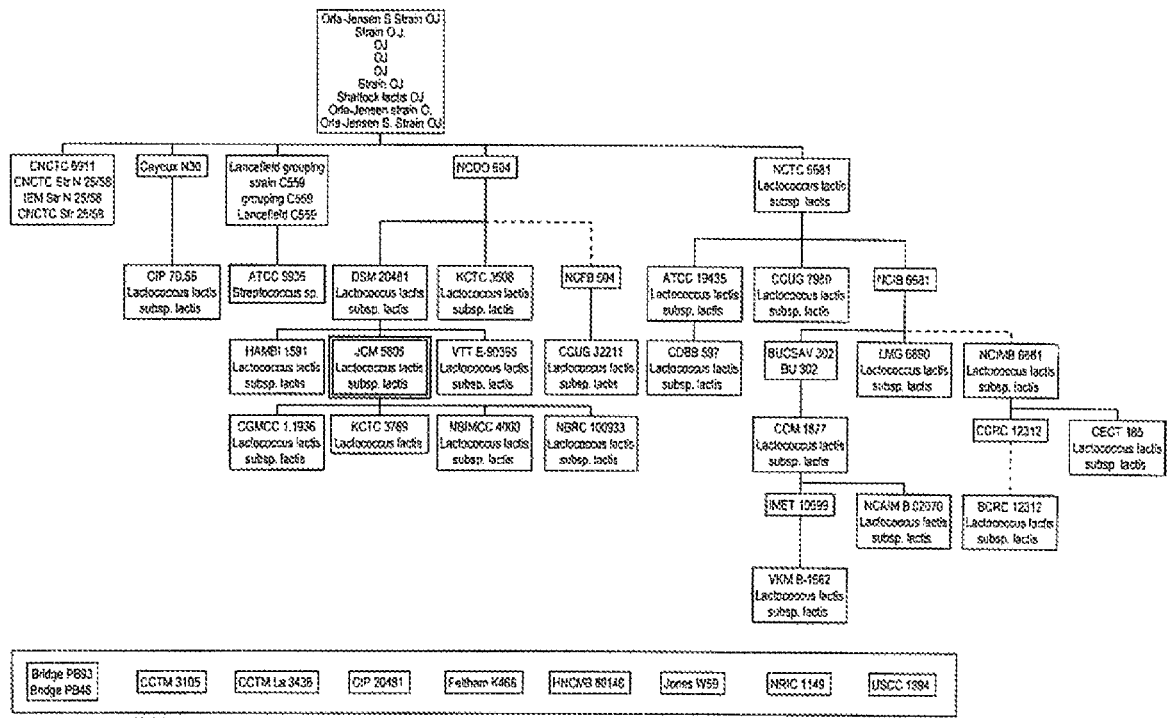
FIG. 1 shows the relationship between *Lactococcus lactis* subsp. *lactis* JCM5805 and a strain equivalent to the JCM5805 strain (a strain derived from the JCM5805 strain and a strain from which the JCM5805 strain is derived).

Among the lactic acid bacterial strains listed above, the JCM bacterial strains are available from the Microbe Division of the RIKEN BioResource Center jcm.brc.riken.jp/ja/); the NBRC bacterial strains are available from the Biological Resource Center (NBRC) at the National Institute of Technology and Evaluation (www.nbrc.nite.go.jp); and the NRIC bacterial strains are available from the Culture Collection Center at Tokyo University of Agriculture (nodaiweb.university.jp/nric/). In addition to the specific bacterial strains listed above, bacterial strains equivalent to *Lactococcus lactis* subsp. *lactis* JCM5805, *Lactococcus lactis* subsp. *lactis* JCM20101, *Lactococcus lactis* subsp. *lactis* NBRC12007, *Lactococcus lactis* subsp. *lactis* NRIC1150, *Lactococcus garvieae* NBRC100934, *Lactococcus lactis* subsp. *cremoris* JCM16167, *Lactococcus lactis* subsp. *cremoris* NBRC100676, *Lactococcus lactis* subsp. *hordniae* JCM1180, and *Lactococcus lactis* subsp. *hordniae* JCM11040 can be used in the present invention. The phrase "equivalent bacterial strains," as used herein, refers to bacterial strains derived from the bacterial strains listed above or bacterial strains from which the bacterial strains listed above are derived or offspring bacterial strains of such bacterial strains. Equivalent bacterial strains may be conserved in other culture collection institutes. FIG. 1 shows bacterial strains derived from *Lactococcus lactis* subsp. *lactis* JCM5805 and bacterial strains from which *Lactococcus lactis* subsp. *lactis* JCM5805 is derived. The bacterial strains equivalent to *Lactococcus lactis* subsp. *lactis* JCM5805 shown in FIG. 1 can also be used as the active ingredient of the present invention. "*Lactococcus lactis* subsp. *lactis* JCM5805," as referred to herein, includes these equivalent bacterial strains. Other lactic acid bacteria usable as the active ingredient of the present invention are available from the Microbe Division of the RIKEN BioResource Center (3-1-1 Koyadai, Tsukuba-shi, Ibaraki), American type culture collection (U.S.A.), the National Institute of Technology and Evaluation (2-5-8 Kazusakamatari, Kisarazu-shi, Chiba), the Culture Collection Center at Tokyo University of Agriculture (1-1-1 Sakuragaoka, Setagaya-ku, Tokyo), and the like.

The *Lactococcus* bacterium, which is the active ingredient of the present invention, may be in the form of a culture product. The term "culture product" refers to a live bacterial cell, a dead bacterial cell, a fragmented live or dead bacterial cell, a lyophilized live or dead bacterial cell, or a fragmented product, culture solution or culture extract of such a lyophilized bacterial cell, and include part of *Lactococcus* bacteria and treated products of *Lactococcus* bacteria. Here, such treated products include those obtained by treating *Lactococcus* bacteria with an enzyme, heat and the like and those recovered through ethanol precipitation of such treated products.

*Lactococcus* bacteria can be cultured by a known method using a known medium. Usable media include MRS, GAM and LM17 media, and an inorganic salt, vitamin, amino acid, antibiotic, serum, or the like can be added to such a medium as appropriate. Culturing may sufficiently be carried out at 25° C. to 40° C. for several hours to several days.

After culturing, *Lactococcus* bacterial cells are collected via centrifugation or filtration. When used as dead bacteria, they may be sterilized and inactivated in an autoclave or the like.

The composition and agent according to the present invention can be each provided as the *Lactococcus* bacterium, alone, which is the active ingredient, or can be each provided as a mixture of the *Lactococcus* bacterium which is the active ingredient with any other component (for example, an excipient). The amount of the *Lactococcus* bacterium to be blended in the composition and agent according to the present invention can be optionally determined depending, for example, on the purpose, intended use, form, dosage form, symptom, body weight and the like, and can be 0.0005% to 99% (w/w), more preferably 0.001% to 50% (w/w) based on the total amount although the present invention is not limited thereto. In the present invention, the agent of the present invention can consist of a *Lactococcus* bacterium, and the composition of the present invention can comprise a *Lactococcus* bacterium and any other component.

The composition and agent of the present invention are each used in improving skin conditions. The meaning of the "skin conditions," as used herein, includes normal skin conditions and deteriorated skin conditions. The skin conditions can be evaluated using either or both of skin redness and skin moisture content as an index. The skin redness can be measured according to publicly known methods (for example, measurement of a red spot value, measurement of a color difference, and measurement of a hemoglobin amount index). Also, the skin moisture content can be measured according to publicly known methods such as measurement of the skin moisture content and measurement of the skin transepidermal water loss. The moisture content can be measured by a capacitance method. Also, the skin transepidermal water loss can be measured by a method of calculating the transpiration from differences in temperature and humidity of moisture passing through the respective sensors, assuming that the moisture evaporated from the skin or a surface of an object diffuses according to the Fick's law.

The "improvement of skin conditions," as used herein, means making skin conditions better, which includes not only improving deteriorated skin conditions, but also preventing further deterioration of the deteriorated skin conditions, and further includes not only improving normal skin conditions, but also preventing deterioration of the normal skin conditions. The improvement of skin conditions can be evaluated using either or both of skin redness and skin moisture content as an index, and, when either or both of a decrease in skin redness and an increase in skin moisture content is/are observed, the skin conditions can be evaluated as having been improved.

In this invention, the "deteriorated skin conditions" means a state where the skin is damaged by a stimulus in daily life. Examples of the stimulus in daily life include external stimuli such as light exposure, changes in drying and humidity, changes in air temperature, and exposure to foreign objects such as natural substances and chemical substances; and disturbances in life habits such as sleep and meals. The deteriorated skin conditions can be evaluated using either or both of skin redness and skin moisture content as an index, and, when either or both of an increase in skin redness and a decrease in skin moisture content is/are observed, the skin conditions can be evaluated as having been deteriorated. Here, the increase in skin redness and the decrease in skin moisture content can be defined based on the normal skin conditions, and increased redness and a decreased moisture content as compared with those of the normal skin represent deteriorated skin conditions. Examples of the deteriorated skin conditions include a state where the skin redness is increased and a state where the skin moisture content is decreased. The state where the skin redness is increased is a reddish state of the skin, including so-called red face and flushed state, and the state where the skin moisture content is decreased is a dry state of the skin. The normal skin conditions can also translate into a state where the skin barrier function works normally. A subject with the normal skin conditions is not or less aware of a desiccated, stretched, flushed or any other skin condition.

Typical examples of the skin conditions to be improved by the composition and agent of the present invention include skin conditions deteriorated by light exposure. The light exposure is normal light exposure in daily life or light exposure beyond the light exposure (e.g., sunburn), including daily light without limitation on the light wavelength, but is preferably ultraviolet light, in particular, light having a wavelength ranging from 315 to 280 nm, called UVB. The light exposure can be identified based on the amount of ultraviolet light delivered, and the light exposure beyond the light exposure in daily life can be defined as light exposure with an amount of ultraviolet light exceeding that in daily life.

The "deteriorated skin conditions," as used herein, can translate into photodermatosis. Thus, the present invention provides a composition for use in treating, preventing and improving photodermatosis and an agent for treating, preventing and improving photodermatosis each comprising a *Lactococcus* bacterium as an active ingredient. The meaning of the "photodermatosis," as used herein, includes solar dermatitis, sunburn, photoaging and photosensitivity.

The composition and agent according to the present invention can be each provided in the form of a pharmaceutical product (for example, pharmaceutical composition), a quasi-drug, a food, a feed or the like, and can be implemented according to the following descriptions.

The *Lactococcus* bacterium which is the active ingredient of the present invention has an effect for improving skin conditions, and thus can be fed or administered to a subject whose skin is damaged or likely to be damaged by daily life, outdoor activities or the like. The target for feeding and administration is not limited to a human, and may be a mammal other than a human (a domestic animal such as a cow or a horse, or a pet animal such as a dog or a cat).

When the *Lactococcus* bacterium which is the active ingredient of the present invention is provided as a food, it can be provided as a food as it is or provided in a state where it is contained in a food. The food thus provided is a food containing an effective amount of the active ingredient of the present invention. The phrase "containing an effective amount" of the active ingredient of the present invention refers to a content of the active ingredient to be taken within a range as will be described later, when a normally-eaten amount of individual foods is ingested. The meaning of the "food," as used herein, includes health foods, functional foods, nutritional supplements, foods with health claims (such as foods for specified health uses, foods with nutrient function claims, and foods labeled with functions), foods for special dietary uses (such as foods for infants, foods for expectant and nursing mothers and foods for sick persons) and supplements. When the *Lactococcus* bacterium which is the active ingredient of the present invention is fed to an animal other than a human, needless to say, the food referred to herein is used as a feed. Briefly, the meaning of the "food," as used herein, includes "feeds."

The *Lactococcus* bacterium which is the active ingredient of the present invention has an effect for improving skin conditions, and thus can be contained in foods taken daily or provided as supplements. Briefly, the composition and agent according to the present invention can be each provided in the form of a food. In this case, the composition and agent according to the present invention can be each provided in the form of a unit package in which the intake amount per meal is predetermined. Examples of the unit package form per meal include forms which define a constant amount using a pack, a package, a can, a bottle and the like. To exert various actions of the composition and agent according to the present invention better, the intake amount per meal can be determined according to the intake amount of the *Lactococcus* bacterium per dose which will be described later. The food of the present invention may be provided in the form of a package on which an explanation about the intake amount is given, or provided together with a document or the like which explains the intake amount.

The predetermined intake amount per meal in the unit package form may be either the effective daily intake amount or an intake amount obtained by dividing the effective daily intake amount into two or more (preferably two or three) portions. Thus, the unit package form of the composition and agent according to the present invention can contain the *Lactococcus* bacterium in the daily intake amount for humans which will be described later, or can contain the *Lactococcus* bacterium in an amount half or one third of the daily intake amount for humans which will be described later. For convenience of feeding, the composition and agent according to the present invention are each preferably provided in "the form of a unit package per meal" in which the intake amount per meal is the effective daily intake amount.

The form of the "food" is not particularly limited, and the food may be provided, for example, in a beverage form, in a semi-liquid or gelled form, or in a solid or powder form. Examples of the "supplement" include tablets manufactured by adding an excipient, a binder and the like to the active ingredient of the present invention, kneading them together and then tableting the kneaded product, and capsule agents in which the active ingredient is encapsulated in a capsule and the like.

The food provided in the present invention is not particularly limited so long as it contains the active ingredient of the present invention, and examples thereof can include non-alcoholic beverages such as refreshing drinks, carbonated drinks, drinks containing fruit juice, drinks containing vegetable juice, drinks containing fruit juice and vegetable juice, cow milk, soybean milk, milk beverages, drink-type yogurt, drink-type jellies, coffee, cocoa, tea drinks, energy drinks, sports drinks, mineral water and flavored water; carbohydrate-containing foods and beverages such as rice, noodles, bread and pasta; various confectioneries such as Western-style confectioneries including cookies, cakes and chocolate, Japanese-style confectioneries including buns with a bean-jam filling and sweet jellies of adzuki beans, candies, gums, yogurt, chilled sweets and frozen sweets including jellies and puddings, and snacks; alcoholic beverages such as whiskey, bourbon, spirit, liqueur, wine, fruit wine, sake (Japanese rice wine), Chinese liquor, shochu (Japanese distilled spirit), beer, non-alcohol beer having an alcohol content of 1% or less, low-malt beer, other miscellaneous liquors and shochu highball; processed products in which eggs are used, processed products of fish and meat (including giblets such as lever) (including rare delicacy), processed foods such as soup, and liquid diets such as high density liquid diets. It should be noted that mineral water includes both of effervescent mineral water and non-effervescent mineral water.

Tea drinks include all of fermented tea, semi-fermented tea and unfermented tea, and examples thereof include black tea, green tea, barley tea, genmai cha (coarse green tea mixed with roasted brown rice), sencha (ordinary green tea), gyokuro cha (refined green tea), hoji cha (roasted green tea), oolong tea, turmeric herbal tea, pu-erth tea, rooibos tea, rose tea, chrysanthemum tea, and herb tea (such as mint tea and jasmine tea).

Examples of fruits used in drinks containing fruit juice and drinks containing fruit juice and vegetable juice include apple, orange, grape, banana, pear, peach, mango, acai, blueberry and plum. Examples of vegetables used in drinks containing vegetable juice and drinks containing fruit juice and vegetable juice include tomato, carrot, celery, pumpkin, cucumber and watermelon.

The intake amount of the *Lactococcus* bacterium which is the active ingredient of the present invention can be determined depending, for example, on the sex, age, and body weight of a target to be fed, conditions, feeding time, dosage form, administration route and other drugs to be combined. When the *Lactococcus* bacterium is fed for the purpose of improving skin conditions, the daily intake amount for humans can be set to 0.5 to 1000 mg, preferably 5 to 500 mg, more preferably 10 to 300 mg, further preferably 10 to 100 mg, especially preferably about 50 mg on the basis of dried bacterial powder. When the *Lactococcus* bacterium is fed for the purpose of improving skin conditions, the daily intake amount for humans can be set to $1\times10^8$ to $1\times10^{14}$, preferably $1\times10^9$ to $1\times10^{13}$, more preferably $1\times10^{10}$ to $1\times10^{12}$, especially preferably about $1\times10^{11}$ on the basis of the number of bacteria. The number of times of feeding is not particularly limited, and the effective intake amount may be fed once daily or fed in several batches. Also, the feeding timing is not particularly limited, and feeding can be performed at a timing when the subject can easily take the *Lactococcus* bacterium. The intake amount and feeding timing of the *Lactococcus* bacterium described above and the feeding period which will be described later are applicable when the *Lactococcus* bacterium which is the active ingredient of the present invention is used for both non-therapeutic and therapeutic purposes, and the "feeding" (intake) can be read as "administration" in the case of therapeutic purposes.

The composition and agent according to the present invention can exert the effect better when fed for a long time, and can be continuously fed, for example for 3 days or more, preferably for 6 days or more, more preferably for 10 days or more. The "continuously," as used herein, means that feeding is continued every day. When the composition and agent according to the present invention are each provided in the package form, packages containing an effective intake amount for a certain period (for example, 1 week) may be provided as a set, for continuous feeding.

The composition and agent according to the present invention each utilize, as an active ingredient, a lactic acid bacterium which is a food material which has been eaten by humans for a long time, and thus have high safety without concerns about side effects even when used continuously. Therefore, the combination of the composition and agent according to the present invention with an existing agent for improving skin conditions can reduce the dose of the existing agent and therefore can alleviate or overcome the side effects of the existing agent. When used in combination with any other agent, the composition and agent according to the present invention may be prepared separately from the other agent, or the other agent and the composition and agent according to the present invention (or the *Lactococcus* bacterium) may be blended together in the same composition.

The composition and agent as well as food according to the present invention may be attached with an indication that they have an effect for improving skin conditions. In this case, the composition and agent as well as food according to the present invention may be attached with some or all of the following indications for better understanding of consumers. Needless to say, the meaning of the phrase "improving skin conditions," as used herein, includes the following indications:

for persons who are anxious about sunburn; and
for persons who are anxious about damage to the skin caused by daily life; and
for persons who are anxious about drying of the skin; and
for persons who are anxious about hot flashes of the skin; and
for persons who are anxious about erythema; and
for persons who are anxious about skin redness; and
for persons who are anxious about red face; and
for persons who are anxious about rough hands; and According to the present invention, there is provided a method for improving skin conditions, comprising feeding or administering an effective amount of a *Lactococcus* bacterium or a composition comprising the same to a subject in need thereof. Also, according to the present invention, there is provided a method for treating, preventing and improving photodermatosis, comprising feeding or administering an effective amount of a *Lactococcus* bacterium or a composition comprising the same to a subject in need thereof. The target for feeding or administration is a mammal including a human, preferably a human. The method for improving skin conditions according to the present invention and the treatment, prevention and improvement method according to the present invention can be carried out according to the descriptions about the composition and agent according to the present invention and the active ingredient of the present invention.

According to the present invention, there is provided use of a *Lactococcus* bacterium or a composition comprising the same, for the manufacture of a composition for use in improving skin conditions or for the manufacture of an agent for improving skin conditions. Further, according to the present invention, there is provided use of a *Lactococcus* bacterium or a composition comprising the same, for the manufacture of a composition for use in treating, preventing and improving photodermatosis, or for the manufacture of an agent for treating, preventing or improving photodermatosis, as an agent for treating, preventing or improving photodermatosis. The use of the present invention can be carried out according to the descriptions about the composition and agent according to the present invention and the active ingredient of the present invention.

Further, according to the present invention, there is provided use of a *Lactococcus* bacterium or a composition comprising the same, for improving skin conditions, as an agent for improving skin conditions, or in the method for improving skin conditions according to the present invention. Furthermore, according to the present invention, there is provided use of a *Lactococcus* bacterium or a composition comprising the same, for treating, preventing or improving photodermatosis, as an agent for treating, preventing or improving photodermatosis, or in the treatment, prevention or improvement method according to the present invention. The use of the present invention can be carried out according to the descriptions about the composition and agent according to the present invention and the active ingredient of the present invention.

Further, according to the present invention, there is provided a *Lactococcus* bacterium or a composition comprising the same, for use in improving skin conditions, or for use in the method for improving skin conditions according to the present invention. Furthermore, according to the present invention, there is provided a *Lactococcus* bacterium or a composition comprising the same, for use in treating, preventing or improving photodermatosis, or for use in the treatment, prevention or improvement method according to the present invention. The *Lactococcus* bacterium and composition comprising the same according to the present invention can be carried out according to the descriptions about the composition and agent according to the present invention and the active ingredient of the present invention.

The method for improving skin conditions according to the present invention and the use of the present invention may be used in mammals including humans, and are intended to involve both of therapeutic use and non-therapeutic use. The "non-therapeutic," as used herein, means elimination of operating, treating or diagnosing activities to a human (i.e., medical activities to a human), and specifically means elimination of a method of performing operation or treatment of, or diagnosis involving, a human by a doctor or a person who receives an instruction from the doctor.

EXAMPLES

Hereinafter, the present invention will be described in more detail by way of the following examples, but is not limited thereto.

Example 1

Effect of Lactic Acid Bacterium (JCM5805) Feeding on Improving Skin Damage (1) Test Method
a. Grouping Four (4)-week-old female mice (HOS: HR-1, Japan SLC, Inc.) were allowed to freely eat a solid feed AIN-93G (manufactured by Oriental Yeast Co., Ltd.), and acclimated and bred for 7 days. The mice after acclimation were divided into four groups. The group which was fed with a normal diet without ultraviolet irradiation was defined as "non-irradiated group" (6 mice). The group which was subjected to ultraviolet irradiation and fed with the normal diet was defined as "normal diet group" (6 mice). The group which was subjected to ultraviolet irradiation and fed with a feed mixture containing *Lactococcus lactis* subsp. *lactis* JCM5805 (hereinafter referred to as JCM5805) was defined as "JCM5805 group" (6 mice). The group which was subjected to ultraviolet irradiation and fed with a feed mixture containing α-tocopherol was defined as "α-TOC group" (6 mice). The average body weight at the beginning of the test was 17.86±1.67 g for the non-irradiated group, 18.89±0.89 g for the normal diet group, 18.48±0.66 g for the JCM5805 group, and 18.26±1.05 g for the α-TOC group, and no significant difference was confirmed among the groups. Since vitamin E was confirmed to be effective in reducing skin disorders induced by ultraviolet light (J. Agric. Food Chem., 2010, 58, 7013-7020, J. Nutr. Sci. Vitaminol. 54, 117-123, 2008), α-tocopherol, which is one of vitamin E, was used as a positive control. During the test period, the mice were fed in individual cages.

b. Test Feed

Simultaneously with the beginning of the test, as test feeds, AIN-93G was freely fed to the non-irradiated group and the normal diet group, and 1 mg of dead and dried powder of JCM5805 or 2.5 mg of α-tocopherol (manufactured by Wako Pure Chemical Industries, Ltd.) was freely fed, as a feed mixture with AIN-93G, to the JCM5805 group and the α-TOC group, respectively, per mice daily. The test feed feeding period was 17 days.

c. Ultraviolet irradiation

On the 14$^{th}$ day from the date of beginning of feeding the test feeds, the mice were irradiated with ultraviolet light. Specifically, a single dose of ultraviolet light (UVB) having a wavelength of 312 nm, corresponding to 90 mJ/cm$^2$ (dose in this test), was delivered. The light source used for irradiation was an oven-type ultraviolet irradiation device DF-312 Donafix (manufactured by ATTO Corporation). In light of the daily integrated UV-B amount in winter at Sapporo (2kJ/m$^2$: Japan Meteorological Agency website: www.data.jma.go.jp/gmd/env/uvhp/uvb_monthave_sap.html), the dose in this test, corresponding to 90 mJ/cm$^2$ (900 J/m$^2$), can be said to be equivalent to the amount of ultraviolet light received in daily life.

(2) Evaluation Method

Before ultraviolet irradiation and 3 days after ultraviolet irradiation, a measurement probe was put on a place near the back midline 2 cm distant from the root of the mouse tail to measure the erythema value, skin moisture content, and skin transepidermal water loss at the back of the mouse. Specific measurement methods will be described below. A multi-probe adapter (MPA5, manufactured by Courage & Khaazaka) was used for connection of the respective probes.

For the erythema value, the concentration of hemoglobin known as an index of redness/ruddy color of the skin was measured using Mexameter MX18 (manufactured by Courage & Khaazaka). Mexameter MX18 measures reflected light from the skin upon irradiation with light having wavelengths of 568 nm and 660 nm from the measurement probe put on the skin, and the measured values are numerically indicated as relative values. The erythema value was measured seven times for each mouse, and an average value of the five measured values, except the maximum and minimum values, was calculated and used as a measured value.

The skin moisture content was measured using Corneometer CM825 (manufactured by Courage & Khaazaka). Corneometer CM825 measures an amount of moisture contained within 15 μm (mainly, in the stratum corneum) from the skin surface as a capacitance by an electric field generated in the skin through the probe tip by the capacitance method, and the measured values are numerically indicated as relative values. The skin moisture content was measured seven times for each mouse, and an average value of the five measured values, except the maximum and minimum values, was calculated and used as a measured value.

The skin transepidermal water loss was measured using Tewameter TM300 (manufactured by Courage & Khaazaka). Tewameter TM300 measures a temperature difference and a humidity difference of moisture passing through temperature/humidity sensors arranged within the probe tip, and measures the skin transepidermal water loss (g/h/m$^2$) from the measured values. In the measurement of the skin transepidermal water loss, the final value when the measurement using the Tewameter was automatically terminated was used as a measured value.

(3) Statistical Analysis

For the measured erythema value, skin moisture content and skin transepidermal water loss, a significance test was conducted among the four groups using the Tukey-Kramer method which is a single-stage multiple comparison test. The significance level was defined as less than 5%.

(4) Results

Figure 2:
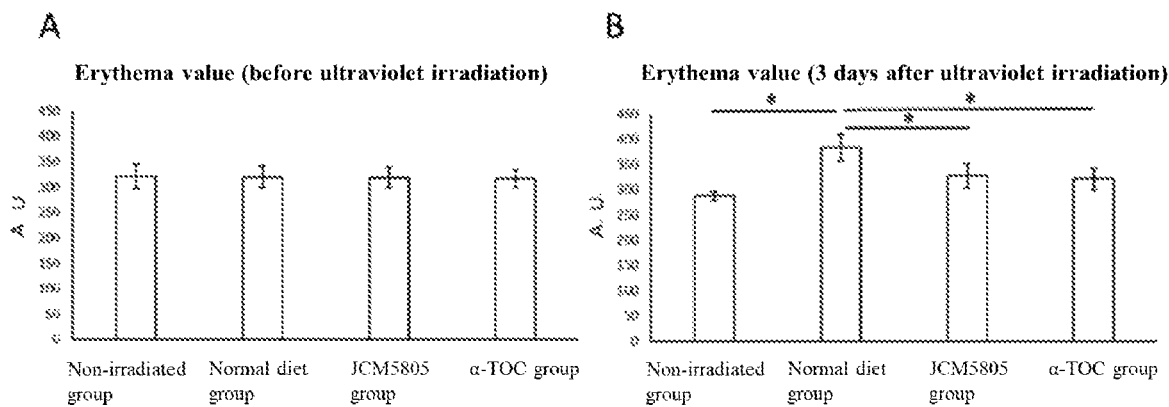
FIG. 2 shows an effect of lactic acid bacterium (JCM5805) feeding on improving skin damage (erythema) in Example 1. A: Graph indicating an erythema value before ultraviolet irradiation. B: Graph indicating an erythema value 3 days after ultraviolet irradiation. The values are each represented by average value±standard deviation. * denotes $p<0.05$ (Tukey-Kramer test).
Figure 3:
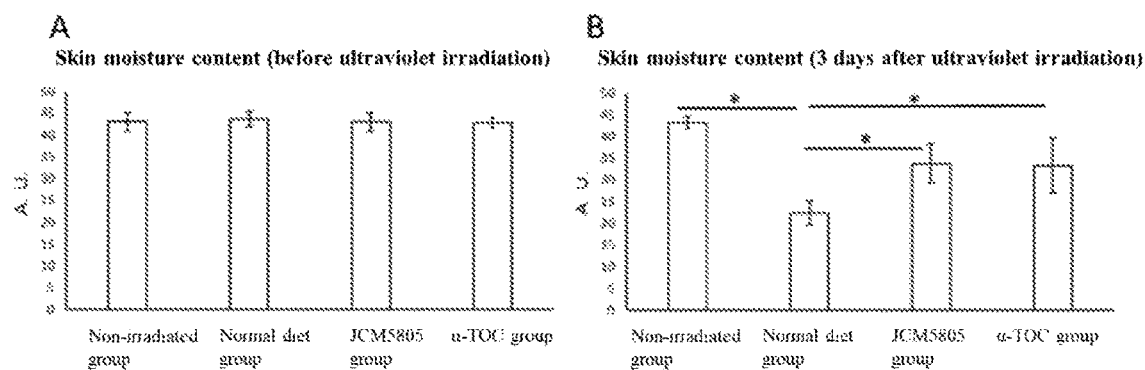
FIG. 3 shows the effect of lactic acid bacterium (JCM5805) feeding on improving skin damage (skin dryness) in Example 1. A: Graph indicating a skin moisture content before ultraviolet irradiation. B: Graph indicating a skin moisture content 3 days after ultraviolet irradiation. The values are each represented by average value±standard deviation. * denotes $p<0.05$ (Tukey-Kramer test).
Figure 4:
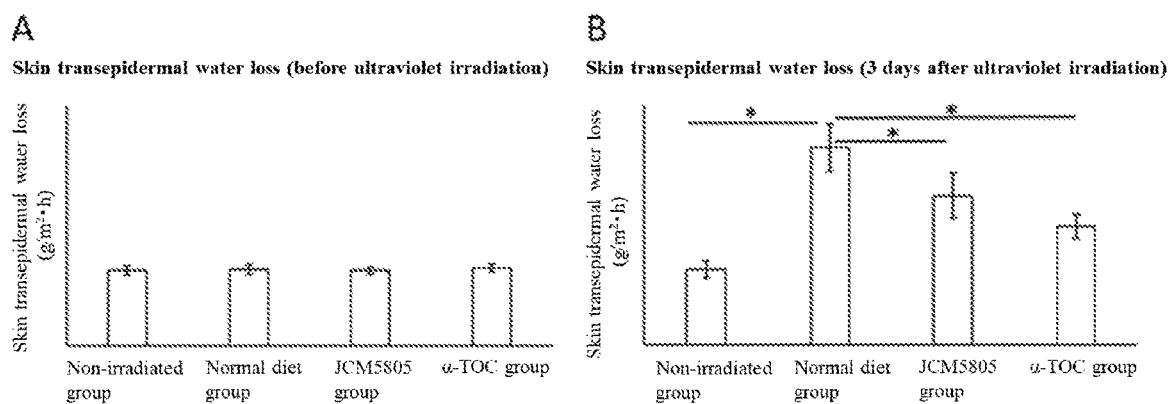
FIG. 4 shows the effect of lactic acid bacterium (JCM5805) feeding on improving skin damage (skin dryness) in Example 1. A: Graph indicating a value of skin transepidermal water loss before ultraviolet irradiation. B: Graph indicating a value of skin transepidermal water loss 3 days after ultraviolet irradiation. The values are each represented by average value±standard deviation. * denotes $p<0.05$ (Tukey-Kramer test).

The results were as shown in FIGS. 2 to 4. As shown in FIG. 2, the erythema value was significantly increased 3 days after ultraviolet irradiation in the normal diet group as compared with the non-irradiated group, but the increase in erythema value was significantly suppressed in the JCM5805 group and the α-TOC group as compared with the normal diet group. As shown in FIG. 3, the skin moisture content was significantly decreased 3 days after ultraviolet irradiation in the normal diet group as compared with the non-irradiated group, but the decrease in skin moisture content was significantly suppressed in the JCM5805 group and the α-TOC group as compared with the normal diet group. As shown in FIG. 4, the skin transepidermal water loss was significantly increased 3 days after ultraviolet irradiation in the normal diet group as compared with the non-irradiated group, but the increase in skin transepidermal water loss was significantly suppressed in the JCM5805 group and the α-TOC group as compared with the normal diet group.

It is known that the increase in erythema value is induced upon application of ultraviolet (UVB) light to the skin, but is improved upon oral feeding of vitamin E (J. Agric. Food Chem., 2010, 58, 7013-7020, J. Nutr. Sci. Vitaminol. 54, 117-123, 2008). As shown in FIG. 2, the improvement effect of α-tocopherol, as the positive control against skin damage caused by ultraviolet irradiation, was confirmed also in this test. From the fact that the intake amount (1 mg/day) of the dead and dried powder of JCM5805 was smaller than the intake amount (2.5 mg/day) of α-tocopherol, but, nevertheless, provided an equivalent improvement effect against ultraviolet light, it was confirmed that the improvement effect on skin damage per unit dose of the dead and dried powder of JCM5805 was confirmed to be higher than the effect of α-tocopherol.

The results demonstrated that the dead and dried powder of JCM5805 have an improvement effect on skin damage which is typified by skin damage caused by UV irradiation, and may have an improvement effect also on skin damage which may usually occur in daily life.

Example 2

Effect of Lactic Acid Bacterium (JCM5805) Feeding on Improving Skin Conditions (1) Preparation of Lactic Acid Bacterium-Containing Food As a lactic acid bacterium-containing food, a hard capsule containing 50 mg ($1.0 \times 10^{11}$ or more cells) of dead and dried powder of JCM5805 and 150 mg of corn starch was prepared. As a placebo food, a hard capsule containing no JCM5805 and 200 mg of corn starch was prepared.

(2) Test Method

Seventy (70) Japanese men and women of thirty years old and over and under sixty years old who were susceptible to skin troubles were adopted as subjects. The subjects were randomly divided into two groups without imbalances in sex, age, BMI, skin symptom evaluation by a doctor (texture visual evaluation, skin quality evaluation and contusion-associated evaluation), or the like. The group to which the lactic acid bacterium-containing food was fed was defined as "test group" (9 men and 26 women, 35 subjects in total), and the group to which the placebo food was fed was defined as "control group" (10 men and 25 women, 35 subjects in total).

In a placebo-controlled randomized double blind test design, as test foods, one capsule containing the lactic acid bacterium-containing food prepared in the above item (1) and one capsule containing the placebo food were continuously fed to the test group and the control group, respectively, once daily for 8 weeks (56 days). During the test period, the subjects were made to continue life habits before the test period.

This test was examined by the Ethical Committee of the Oriental Ueno Kenshin Center, obtained approval, and then was conducted. The test was conducted in compliance with the Ethical Principles Based on the Declaration of Helsinki and "Ethical Guidelines for Medical and Health Research Involving Human Subjects" (Ministry of Education, Culture, Sports, Science and Technology and Ministry of Health, Labour and Welfare).

(3) Evaluation Method

The change in skin redness was evaluated as an index of skin conditions before and after feeding of the test foods. Specifically, before the beginning of the test period (8 weeks) (hereinafter referred to "before the test period" in some cases) and at the end of the test period (hereinafter "after the test period" in some cases), the measurement probe was put on the center part between a part under the earlobe and the lip end on the subject's left face to measure the color difference and hemoglobin amount index (hereinafter referred to as "Hb index" in some cases). The color difference and Hb index were measured using a spectroscopic calorimeter (CM-2600d, manufactured by Konica Minolta, Inc.) and analyzed by analysis software (CM-SA, manufactured by Konica Minolta, Ltd.). Each measurement was carried out five times at the same site of each of the subjects to obtain L*, a* and b* values and Hb index. Of the five values measured for each of the L*, a* and b* values and Hb index, an average value of the three values except the values when the L* value was maximum or minimum was calculated and used as a measured value. The measured values before and after the test period were evaluated by the paired t-test. The L* value is a parameter representing the lightness, and it is known that the color is closer to white (light) when the measured value is higher, and closer to black (dark) when the measured value is lower. The a* value is a parameter representing red to green, and it is meant that the color is closer to red when the measured value is higher and closer to green when the measured value is lower. The b* value is a parameter representing yellow to blue, and it is known that the color is closer to yellow when the measured value is higher, and closer to blue when the measured value is lower. Also, the Hb index is known to be an index of skin redness.

(4) Results

During the test period, 2 subjects dropped out, and thus 33 subjects in the test group and 35 subjects in the control group were adopted as the target for analysis. The results were as indicated in Table 1.

TABLE 1

Measurement results of color difference and Hb index

| Measurement Item | Group | Measured value (average value ± standard deviation) | | P value |
|---|---|---|---|---|
| | | Before test period (at Week 0 of test) | After test period (at Week 8 of test) | |
| L* value | Test group | 64.46 ± 3.46 | 64.81 ± 2.93 | |
| | Control group | 64.79 ± 2.89 | 64.93 ± 2.51 | |
| a* value | Test group | 7.38 ± 1.46 | 6.83 ± 1.44 | P < 0.01 |
| | Control group | 7.00 ± 1.71 | 6.64 ± 1.29 | |
| b* value | Test group | 17.20 ± 2.28 | 17.03 ± 2.33 | |

TABLE 1-continued

Measurement results of color difference and Hb index

| Measurement Item | Group | Measured value (average value ± standard deviation) | | P value |
|---|---|---|---|---|
| | | Before test period (at Week 0 of test) | After test period (at Week 8 of test) | |
| | Control group | 16.62 ± 2.55 | 16.22 ± 2.44 | |
| Hb index | Test group | 1.03 ± 0.23 | 0.95 ± 0.25 | P < 0.01 |
| | Control group | 1.01 ± 0.28 | 0.97 ± 0.22 | |

As indicated in Table 1, the L* and b* values were not significantly changed in the test group or the control group in the comparison between before and after feeding. The a* value (parameter representing red to green) and Hb index were unchanged in the control group, but confirmed to be significantly decreased in the test group (p<0.01). These results confirmed that feeding of the food containing the lactic acid bacterium JCM5805 decreases and improves skin redness. In other words, feeding of the food containing the lactic acid bacterium (JCM5805) was confirmed to have an effect for improving skin conditions.

The invention claimed is:

1. A method for improving skin conditions in a subject in need thereof, comprising feeding or administering to the subject (a) an effective amount of a *Lactococcus* bacterium or (b) a composition comprising an effective amount of the *Lactococcus* bacterium as an active ingredient, wherein the *Lactococcus* bacterium is *Lactococcus lactis* subsp. *lactis* JCM5805.

2. The method according to claim 1, wherein the skin conditions are skin conditions deteriorated by light exposure.

3. The method according to claim 2, wherein the skin conditions deteriorated by light exposure are a decrease in skin moisture content and/or an increase in skin redness.

4. The method according to claim 1, wherein the composition comprises the Lactococcus bacterium in the form of a dead bacterium.

5. The method according to claim 1, wherein the *Lactococcus* bacterium is fed or administered at an effective daily intake amount for a human.

6. The method according to claim 5, wherein the effective daily intake amount for a human ranges from 0.5 to 1000 mg of dried powder of the *Lactococcus* bacterium.

7. The method according to claim 5, wherein the effective daily intake amount for a human ranges from $1 \times 10^8$ to $1 \times 10^{14}$ of the *Lactococcus* bacterium.

8. The method according to claim 1, wherein the composition comprises an effective daily intake amount of the Lactococcus bacterium for a human.

9. The method according to claim 8, wherein the effective daily intake amount for a human ranges from 0.5 to 1000 mg of dried powder of the *Lactococcus* bacterium.

10. The method according to claim 8, wherein the effective daily intake amount for a human ranges from $1 \times 10^8$ to $1 \times 10^{14}$ of the *Lactococcus* bacterium.

11. The method according to claim 1, wherein the composition is in the form of a unit package.

12. The method according to claim 1, wherein the composition is a food composition.

13. The method according to claim 1, wherein the skin conditions are deteriorated skin conditions.

14. The method according to claim 13, wherein the deteriorated skin conditions are a decrease in skin moisture content and/or an increase in skin redness.

\* \* \* \* \*